United States Patent [19]

Chauveau et al.

[11] Patent Number: 6,106,861
[45] Date of Patent: *Aug. 22, 2000

[54] MULTIPARTICULATE TABLET DISINTEGRATING IN LESS THAN 40 SECONDS IN THE MOUTH

[75] Inventors: Charles Chauveau, Valbonne; Edouard Gendrot, Garnay; Alain Gilles Demichelis, Grasse; Noureddine Nouri, Vallauris, all of France

[73] Assignee: Laboratoires Prographarm, Chateauneuf en Thymerais, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/985,793

[22] Filed: Dec. 5, 1997

[30] Foreign Application Priority Data

Jul. 21, 1997 [FR] France .................................. 97 09233

[51] Int. Cl.$^7$ .............................. A61K 9/20; A61K 9/14; A61K 9/16
[52] U.S. Cl. ......................... 424/465; 424/494; 424/497; 514/960
[58] Field of Search ..................................... 424/464, 465, 424/470, 474, 479, 489, 493, 494, 497, 469; 514/960

[56] References Cited

U.S. PATENT DOCUMENTS

| 2,887,437 | 3/1959 | Kloza et al. . |
| 3,488,418 | 1/1970 | Holliday et al. . |
| 3,524,910 | 8/1970 | Holliday et al. . |
| 3,882,228 | 5/1975 | Boncey et al. . |
| 4,016,254 | 4/1977 | Seager . |
| 4,017,598 | 4/1977 | Ohno et al. . |
| 4,371,516 | 2/1983 | Gregory et al. . |
| 4,547,359 | 10/1985 | Zicrenberg et al. . |
| 4,574,080 | 3/1986 | Roswall et al. . |
| 4,666,703 | 5/1997 | Kopf . |
| 4,687,662 | 8/1987 | Schobel . |
| 4,710,384 | 12/1987 | Rotman . |
| 4,760,093 | 7/1988 | Blank et al. . |
| 4,832,956 | 5/1989 | Gergely et al. . |
| 4,851,226 | 7/1989 | Julian et al. . |
| 4,867,987 | 9/1989 | Seth . |
| 4,874,614 | 10/1989 | Becker . |
| 4,886,669 | 12/1989 | Ventouras . |
| 4,904,477 | 2/1990 | Ho et al. . |
| 4,915,953 | 4/1990 | Jordan et al. . |
| 4,940,588 | 7/1990 | Sparks et al. . |
| 5,047,247 | 9/1991 | Milovac et al. . |
| 5,073,374 | 12/1991 | McCarty et al. . |
| 5,073,377 | 12/1991 | Alexander et al. . |
| 5,178,878 | 1/1993 | Wehling et al. . |
| 5,198,228 | 3/1993 | Urban et al. . |
| 5,215,756 | 6/1993 | Cole et al. . |
| 5,464,632 | 11/1995 | Cousin et al. . |
| 5,576,014 | 11/1996 | Mizumoto et al. . |
| 5,629,016 | 5/1997 | Fieldman et al. . |

FOREIGN PATENT DOCUMENTS

| 49161/85 | 10/1985 | Australia . |
| 79507/87 | 10/1987 | Australia . |
| 33946/89 | 5/1989 | Australia . |
| 66012/90 | 9/1990 | Australia . |
| 72560/91 | 2/1991 | Australia . |
| 052076 B1 | of 0000 | European Pat. Off. . |
| 250648 A2A3 | of 0000 | European Pat. Off. . |
| 003589 A2 | 2/1979 | European Pat. Off. . |
| 196546 A2 | 2/1979 | European Pat. Off. . |
| 207041 A2 | 6/1986 | European Pat. Off. . |
| 255002 A1 | 7/1987 | European Pat. Off. . |
| 266113 | 10/1987 | European Pat. Off. . |
| 273005 A1 | 11/1987 | European Pat. Off. . |
| 281200 A1 | 2/1988 | European Pat. Off. . |
| 313328 A1 | 10/1988 | European Pat. Off. . |
| 347767 A1 | 6/1989 | European Pat. Off. . |
| 350701 | 6/1989 | European Pat. Off. . |
| 408273 A1 | 7/1990 | European Pat. Off. . |
| 1134097 | 1/1968 | United Kingdom . |
| 154022 | 7/1979 | United Kingdom . |
| 2067900 | 1/1980 | United Kingdom . |
| 2086725 | 8/1985 | United Kingdom . |
| 2087235 | 11/1990 | United Kingdom . |
| WO91/04757 | 4/1991 | WIPO . |
| WO91/16043 | 10/1991 | WIPO . |

OTHER PUBLICATIONS

Lehman, K., "Formulation of Controlled Release Tablets with Acrylic Resins" Acta. Pharma. Fenn. 93, pp. 55–74 (1984).

Lehman, K.O.R. , "Chemistry & Application Properties of Polymethacrylate Coating Systems" in Aqueous Polymeric Coatings for Pharmaceutical Dosage Forms (J.W. McGinity, ed.) pp. 222–234, Marcel Dekker Inc., New York (1989).

(List continued on next page.)

Primary Examiner—Thurman K. Page
Assistant Examiner—Brian K. Seidleck
Attorney, Agent, or Firm—Caesar, Rivise, Bernstein, Cohen & Pokotilow, Ltd.

[57] ABSTRACT

The invention relates to a rapidly disintegratable multiparticulate tablet which disintegrates in the mouth in less than 40 seconds and which comprises an excipient and an active ingredient in the form of microcrystals coated with a coating agent. The excipient comprises, with respect to the mass of the tablet, from 3 to 15% by weight of at least one disintegration agent and from 40 to 90% by weight of at least one soluble diluent agent with binding properties consisting of a polyol having less than 13 carbon atoms, said polyol being either in the directly compressible form which is composed of particles whose average diameter is from 100 to 500 micrometers or in the powder form which is composed of particles whose average diameter is less than 100 micrometers, said polyol being selected from the group consisting of mannitol, xylitol, sorbitol and maltitol, with the proviso that, when only one soluble diluent agent with binding properties is used, it is a polyol in the directly compressible form except sorbitol and, when at least two soluble diluent agents with binding properties are used, one is consisting of a polyol in the directly compressible form and the other is consisting of the same or another polyol in powder form, the proportion of directly compressible polyol to powder polyol being from 99/1 to 50/50.

12 Claims, No Drawings

OTHER PUBLICATIONS

Butterworth's Medical Dictionary, 2$^{nd}$ Edition (1978) Butterworths, London, ISBN 0 407 00193 X; p. 1449.

Remington's Pharmaceutical Sciences, 18$^{th}$ Edition (1990) "Disintegrants", Mack Publishing Co, ISBN 0–912734–04–3, p. 1637.

Remington's Pharmaceutical Sciences, Mack Publishing Co. pp. 1604–1605 (1975).

Pharmaceutical Dosage Forms, vol. 1, ed. Lieberman & Lachman, Marcel Decker, Inc., ISBN 0–8247–6918–X (1980), pp. 72–88, 135–136, 289–294.

Pharmaceutical Dosage Forms, vol. 1, ed. Lieberman & Lachman, Marcel Decker, Inc., ISBN 0–8247–6918–X (1980), pp. 135–141.

J. Putter, Med. Welt, Bd. 27/Heft 28, pp. 1362–1365 (1976) (and English Translation).

Rote Liste 1982, 78 002 (and English Translation).

Beipackzettel Colfarit, Sep. 1987 (and English Translation).

Auszug aus der Herstellungvorschrift fur Colfarit, gutig ab Jun. 19, 1990 with the abstract Apr. 4, 1991 gutigen Zefallstest (and English Translation).

"Tablettieren" "verpressen von uberzognen Partikein zu zerfallenden Tabletten mit knotrollerter Wirkstoffabgabe" of 09.05–11.05–1990 (and English Translation).

Duchene, D. "Tablet disintegration" in Topics in Pharmaceutical Sciences, (1983), (D.D. Bremer and P. Speiser, eds) p. 387–399, Elsevier Science Publishers, Amsterdam, New York and Oxford (and English Translation).

NYMCEL brochure, 6 pages, undated.

The Theory & Practice of Industrial Pharmacy, Lea & Febiger, pp. 320–321, , 325–328, 412–429 (1986).

Merck Index, pp. 6, 114, 156, 247, 248, 649 1109 (1976).

Article Pharm. Ind. 48, Saki, p. 92–94 (1986).

Manufacturing Chemist and Aerosol News, Apr. 1977, Seager, pp. 25–35.

Manufacturing Chemist, Mar. 1982, pp. 31–33, Lang.

International Journal of Pharmaceutics, 41, 159–167, Wan (1980).

Pharm. Dosage Forms vol. 1, Chap. 2 pp. 86–88, Lieberman (1980).

Pharm. Dosage Forms vol. 1, Chap. 3 pp 135–141, Lieberman (1980).

Chemical Technology Review No. 73, Gutcho (1976).

J. Pharmaceut, Sci., 68, 206–211 Lerk et al. (1979).

Ed. Marcel Dekker, Inc., New York pp. 359–403, Marshall (1979).

Amer. Pharm. Assoc. and the Pharm. Society of Great Britain pp. 369–375, Handbook of Pharm. Excip. (1986).

Manuf. Chemist & Aerosol News, Jan. 1976 pp. 25–26, Khan.

Congress of Pharm. Sciences Sept. 5–9, 1983, pp. 387–399 "Tablet disintegration", Duchene.

Ed. Marcel Dekker, New York (1989) pp. 153–245, Lehmann.

Ed. Marcel Dekker, New York pp. 1–33, 161–179, 279–287, Deasy (1984).

Chem. Technology Rev. No. 135, Gutcho (1979).

Microencapsulation: Processes and Applications, Vandegaer (1974).

Microencapsulation, Drugs, and the Pharm. Sciences, vol. 3, Nixon (1976).

Pharm. Technology—Controlled Drug Release, vol. 2 p. 152–152, Oraceska (1991).

Pharm. Dosage Forms vol. 1, Chapter 8, p. 372–376, Lieberman (1989).

Pharm. Dosage Forms, vol. 3, pp. 110 and 157–164, Lieberman (1982).

Pharm. Dosage Forms, vol. 1, pp. 284–286, Lieberman.

Pharm. Dosage Forms, vol. 2, pp. 219–220, Lieberman (1990).

Chem. Pharm. Bull 38(3), 752–756, Yuasa (1990).

Drug. Devel. and Ind. Pharmacy, 12(4), p. 577–587, Abdel Monen Sayed (1986).

Journ. of Pharm. Sc., 73 (Jan) pp. 52–54, Nixon (1984).

Journ. of Pharmacy and Pharmacology, 29 (Mar), pp. 169–173, Jalsenjak (1977).

Journ. of Pharmacy and Pharmacology, 32, pp. 678–680, Jalsenjak (1980).

Acta Pharm. Fenn, 93, 55, Seminar 7 (Feb. 1984).

Drug Devel. and Ind. Pharmacy, 15, 2049–2053, Prapaitrakul (1989).

Pharm. Pelletization Technology (1989) pp. 1–11, 86–105, 187–215.

MULTIPARTICULATE TABLET DISINTEGRATING IN LESS THAN 40 SECONDS IN THE MOUTH

The invention relates to an improved rapidly disintegratable multiparticulate tablet of the type which disintegrates in the mouth in less than 40 seconds and which comprises, on the one hand, an active ingredient in the form of microcrystals coated with a coating agent and, on the other hand, an excipient.

The active ingredient may be selected from the group comprising antalgesics, antipyretics, antidiarrheals, antispasmodics, digestive motoricity regulators and anti-inflammatories and more particularly from the group comprising paracetamol, ibuprofen, aspirin, ketoprofen and loperamide.

French Patent FR 91 09245 discloses multiparticulate tablets of the type in question which are generally satisfactory; however, the texture of some of these tablets leads to a gritty and pasty sensation on ingestion.

The object of the invention is above all to overcome this drawback and to supply a rapidly disintegratable tablet with a systematically pleasant texture, this tablet also leading to an optimum biological availability of the active ingredient.

The Applicants have had the merit of discovering, following extensive research, that this object could be achieved on the one hand by incorporating into the excipient a disintegration agent and at least one particular soluble diluent agent with binding properties and, on the other hand, by selecting the coating agent as a function of the physico-chemical characteristics of the active ingredient.

As a result, the improved multiparticulate tablet according to the invention, which disintegrates in the mouth in less than 40 seconds and which comprises, on the one hand, an active ingredient in the form of coated microcrystals and, on the other hand, an excipient, is characterized in that the excipient comprises at least one disintegration agent and at least one soluble diluent agent with binding properties consisting of a polyol having less than 13 carbon atoms either in the form of the directly compressible product with an average particle diameter of between 100 and 500 micrometres, or in the form of a powder the average particle diameter of which is less than 100 micrometers, this polyol preferably being selected from the group comprising mannitol, xylitol, sorbitol and maltitol, it being understood that sorbitol cannot be used alone and that, when there is a single soluble diluent agent with binding properties, it is used in the form of the directly compressible product whereas, when there are at least two soluble diluent agents with binding properties, one is in the directly compressible form and the other in the form of a powder, it being then possible that the polyol is the same, the proportion of directly compressible polyol to powder polyol being from 99/1 to 50/50 and preferably from 80/20 to 50/50 and the coating of the microcrystals of active ingredient comprises at least one coating agent selected, as a function of the physico-chemical characteristics of the active ingredient, from the group comprising polymethacrylates, cellulose polymers, in particular ethyl celluloses, hydroxypropyl-methyl celluloses, hydroxypropyl celluloses and cellulose acetophthalates and combinations of these polymers with each other optionally combined with plastifiers or soluble agents, in particular polyols.

The invention will be better understood using the additional description and non-limitative examples relating to advantageous methods of implementation which follow.

With the intention of preparing a multiparticulate tablet of the type in question, the procedure is as follows or in an equivalent fashion.

First the active ingredient is selected from the group comprising antalgesics, antipyretics, antidiarrheals, antispasmodics, digestive motoricity regulators and anti-inflammatories and more particularly from the group comprising paracetamol, ibuprofen, aspirin, ketoprofen and loperamide.

The excipient is prepared by mixing at least one disintegration agent with at least one soluble diluent agent with binding properties consisting of a polyol having less than 13 carbon atoms either in the form of a directly compressible product the average particle diameter of which is from 100 to 500 micrometres or in the form of a powder the average particle diameter of which is less than 100 micrometres, this polyol preferably being selected from the group comprising mannitol, xylitol, sorbitol and maltitol, it being understood that sorbitol cannot be used alone.

When there is a single soluble diluent agent with binding properties, therefore different from sorbitol, it is used in the form of a directly compressible product.

When at least two soluble diluent agents with binding properties are used, one is present in the form of the directly compressible product and the other, which can be the same polyol, is in the form of a powder the average component particle diameter of which is less than 100 micrometres, the proportion of directly compressible polyol to powder polyol being from 99/1 to 50/50 and preferably from 80/20 to 50/50.

The disintegration agent is preferably selected from the group comprising cross-linked polyvinylpyrrolidone, designated in the art by the term crospovidone and cross-linked sodium carboxymethylcellulose designated in the art by the term sodium croscarmellose.

The respective proportions of disintegration agent and binding agent or soluble diluent used for the constitution of the excipient are, with respect to the mass of the tablet, from 3 to 15% by weight, preferably from 5 to 10% by weight for the first and from 40 to 90% by weight, preferably from 50 to 70% by weight for the second; the maximum proportion of sorbitol is 30% by weight.

The active ingredient which is a component of the composition of the tablet according to the invention is presented before coating in the form of microcrystals the average diameter of which is from approximately 1 to approximately 500 micrometres.

In the case of certain active ingredients, microcrystals with an average diameter of less than 100 micrometres are preferably used in order to increase the exchange surface between the active ingredient and the ambient environment; by proceeding in this way, the solubilization speed and/or the intrinsic solubility of dissolution are optimized.

The microcrystals are preferably coated using the technique known as the fluidized bed.

Direct coating is applied in the case of microcrystals having an average size of 100 to 500 micrometres; for microcrystals smaller than 100 micrometres, a prior treatment is carried out consisting either in the granulation of the microcrystals by a standard wet or dry granulation process, or by prior fixing of the microcrystals on neutral supports known in themselves when the average size of said microcrystals is less than approximately 20 micrometres; the microcrystals are fixed to the neutral supports in a standard manner using a binding agent consisting for example of hydroxypropylmethyl cellulose.

The coating is obtained from at least one coating agent selected, according to the physico-chemical characteristics of the active ingredient, from the group comprising the polymethacrylates, in particular certain of those marketed under the EUDRAGIT trade mark and more particularly the 30% dispersions of poly(ethylacrylate-methyl-metacrylate) marketed under the trade mark EUDRAGIT NE 30 D, the type E aminoalkyl-methacrylate copolymers marketed under the trade mark EUDRAGIT E, the cellulose polymers, in particular the ethyl celluloses, hydroxypropyl-methyl celluloses, hydroxypropyl celluloses and the cellulose acetophthalate, the combinations of these polymers with each other and optionally in association with plastifiers, for example polyethyleneglycol 6000, or with soluble agents, in particular polyols, for example mannitol.

As an example, the coating can be constituted starting from

EUDRAGIT NE 30 D alone or mixed with EUDRAGIT E in one or more organic solvents, ethyl cellulose alone or mixed with hydroxypropyl-methyl cellulose in association with a plastifier optionally in the presence of a hydroalcoholic solvent, a polymethacrylate, in particular EUDRAGIT NE 30 D mixed with a soluble cellulose derivative, in particular hydroxypropyl-methyl cellulose and a plastifier and/or a soluble diluent agent with binding properties, EUDRAGIT E 100 alone.

Due to the coating according to the invention of the microcrystals of active ingredient, said coating comprising in particular a in association or combination a soluble polymer and an insoluble polymer, the definitive tablet is characterized in that on the one hand, in an acid medium with a pH lower than 5, the quantity of active ingredient which is dissolved, after disintegration of the tablet, in 5 to 20 minutes from the coated microcrystals is equal to at least 80% and preferably to at least 100% of the quantity of active ingredient which is dissolved in the same time period following disintegration from a tablet allowing the immediate release of the active ingredient consisting of microcrystals but in which said microcrystals are not coated and, on the other hand, the active ingredient does not dissolve significantly after remaining for a period of less than 5 minutes in a medium the pH conditions of which are similar to those of saliva, namely 7.0±0.5, thus ensuring satisfactory masking of its taste.

When the quantity of active ingredient which is dissolved after disintegration of the tablet in 5 to 20 minutes from the coated microcrystals is equal to at least 100% of the quantity of active ingredient which is dissolved in the same time period after disintegration from a tablet allowing the immediate release of the active ingredient consisting of microcrystals but in which said microcrystals are not coated, the biological availability of the active ingredient is at least equivalent to that of the same active ingredient obtained from the above tablet in which said microcrystals are not coated.

For the production of the tablet, a mixture of the excipient and the coated microcrystals is first prepared and this mixture is then homogeneized in a dry mixer.

Preferably, a sweetener, a flavouring and a lubricant are incorporated to this mixture.

The sweetener can be selected from the group comprising Aspartame and sodium sacchariante, and the lubricant from the group comprising magnesium stearate, sodium stearylfumarate, stearic acid and polyethyleneglycol 6000.

The mixture is then subjected to a compression force sufficient to confer on the resulting tablet a sufficient hardness for it to be handled and packaged industrially, then carried and handled by the patient without any particular precautions; for information only, it is indicated that the hardnesses meeting these conditions are generally comprised between 20 and 70 Newtons.

The tablets according to the invention present, with respect to the tablets of the type in question which already exist, simultaneously an improvement in the speed at which the active ingredient is made available in the organism and an improvement in palatability.

EXAMPLE 1

Multiparticulate paracetamol tablet dosed at 500 mg.

The composition of the above tablet results from Table I below.

TABLE I

| Constituents | Centesimal formula |
| --- | --- |
| Coated paracetamol | 39.2 |
| Mannitol for direct compression | 36.7 |
| Crystalline powder mannitol | 12.3 |
| Crospovidone | 8.6 |
| Aspartame | 2.7 |
| Blackcurrant flavouring | 0.4 |
| Magnesium stearate | 0.1 |
| Total | 100.0% |

This tablet is prepared as indicated below.

The paracetamol microcrystals are introduced into a fluidized bed installation and a dispersion in ethanol of EUDRAGIT E 100, EUDRAGIT NE 30 D and colloidal silica is sprayed onto the microcrystals in order to obtain microcrystals coated with 10% of polymer.

All the excipients are sieved and the mixture containing the coated paracetamol and the excipients is homogenized in a dry mixer.

The mixture is divided and moulded on a tableting machine equipped with 17 mm diameter punches.

The compression force is adjusted in order to obtain tablets having a hardness of 40±10 Newtons.

The disintegration time in the mouth of the tablets thus obtained is less than 40 seconds.

This time corresponds to the time which separates, on the one hand, the moment the tablet is placed in contact with the saliva in the mouth and, on the other hand, the moment the suspension, resulting from the disintegration of the tablet in contact with the saliva, is swallowed.

The disintegration time less than 40 seconds indicated above is the average of the values noted for a representative group of healthy subjects.

The pharmacokinetic study to which the above tablet was subjected shows that the biological availability of the active ingredient, namely paracetamol, is not significantly different from that which is observed after administration of a commercially available tablet based on paracetamol. The masking of the taste of the paracetamol by the coating present on the tablet according to the invention does not therefore result in any delay in absorption, which is even slightly more rapid as the maximum is achieved in 0.5 hour on average whereas it is only achieved in 0.88 hour on average in the case of the commercially available reference tablet.

The values recorded with respect to the properties of the tablet according to the invention and those relating to a currently marketed paracetamol-based tablet with immediate release of the active ingredient and not previously coated are shown in Table II below.

TABLE II

| Parameters | Tablet containing a 500 mg dose of paracetamol according to the invention | Commercially available tablet containing a 500 mg dose of paracetamol |
|---|---|---|
| Lag t (h) | 0.17 | 0.17 |
| tmax (h) | 0.50 | 0.88 |
| Cmax ($\mu$g/ml) | 6.28 ± 1.61 | 6.26 ± 2.37 |
| AUC0-t ($\mu$g · h/ml) | 18.59 ± 3.44 | 18.10 ± 3.40 |
| AUCinf ($\mu$g · h/ml) | 19.68 ± 3.85 | 19.24 ± 3.79 |

In this table, lag t designates the time in hours which elapsed between the administration of the medicament and the detection of the active ingredient in the subject's blood, tmax designates the time in hours after which the serous concentration of active ingredient reaches a maximum, Cmax ($\mu$g/ml) designates the value of the maximum concentration of active ingredient reached at the value tmax; this concentration is expressed in jug of active ingredient per ml of serum, AUC0-t designates the surface area under the curve of the serous concentrations of active ingredient as a function of time until the last quantified sample is taken, and AUCinf designates the surface area under the curve of the serous concentrations of active ingredient as a function of time extrapolated to infinity.

An examination of the results shown in Table II shows that the coating used to mask the taste of the active ingredient does not result in a modification of the biological availability of the active ingredient or any delay in absorption, which is a determining result in the administration of certain active ingredients where rapid action is desired, in particular antalgesics.

EXAMPLE 2

Multiparticulate loperamide tablet at a dose of 2 mg.

The composition of the above tablet results from Table III below.

TABLE III

| Constituents | Centesimal formula |
|---|---|
| Coated loperamide | 15.1 |
| Mannitol for direct compression | 56.6 |
| Crystalline powder mannitol | 18.8 |
| Crospovidone | 5.0 |
| Aspartame | 3.0 |
| Mint flavouring | 0.7 |
| Magnesium stearate | 0.8 |
| Total | 100.0% |

This tablet is prepared in the manner indicated in Example 1.

The active ingredient is presented in the form of microcrystals the average size of which is less than 20 micrometres; consequently, fixing of these microcrystals on neutral supports consisting of a polyol and having an average size of the order of 60 micrometres is carried out using a hydroxypropyl-methyl cellulose solution.

The neutral supports comprising the loperamide microcrystals are then coated with 20% of a mixture of EUDRAGIT NE 30 D and EUDRAGIT E 100.

This tablet has a hardness of 30±5 Newtons.

It disintegrates in the mouth in 20 seconds.

EXAMPLE 3

Ketoprofen tablet at a dose of 12.5 mg.

The composition of the above tablet results from Table IV below.

TABLE IV

| Constituents | Centesimal formula |
|---|---|
| Coated ketoprofen | 6.7 |
| Mannitol for direct compression | 63.3 |
| Crystalline powder mannitol | 22.2 |
| Crospovidone | 5.0 |
| Aspartame | 1.3 |
| Mint flavouring | 0.7 |
| Magnesium stearate | 0.8 |
| Total | 100.0% |

It is prepared in the manner indicated in Example 2.

The active ingredient is presented in the form of microcrystals the average size of which is less than 20 micrometres; consequently, fixing of these microcrystals on neutral supports consisting of a polyol and the size of which is of the order of 60 micrometres is carried out using a hydroxypropyl-methyl cellulose solution.

The neutral supports comprising the ketoprofen microcrystals constituting the above tablet are then coated with 20% of a mixture of EUDRAGIT NE 30 D, hydroxypropyl-methyl cellulose and polyethylene-glycol 6000.

It has a hardness of 35±5 Newtons.

It disintegrates in the mouth in 20 seconds.

EXAMPLE 4

Multiparticulate acetylsalicylic acid tablet at a dose of 325 mg.

The composition of the above tablet results from Table V below.

TABLE V

| Constituents | Centesimal formula |
|---|---|
| Coated acetylsalicylic acid | 37.4 |
| Mannitol for direct compression | 38.0 |
| Crystalline powder mannitol | 12.6 |
| Crospovidone | 8.6 |
| Aspartame | 2.9 |
| Sodium stearylfumarate | 0.5 |
| Total | 100.0% |

This tablet is prepared in the manner indicated in Example 1.

The acetylsalicylic acid microcrystals constituting the above tablet are coated with 4.5% of ethyl cellulose N7 and polyethyleneglycol 6000.

The tablet has a hardness of 50±15 Newtons.

It disintegrates in the mouth in 20 seconds.

EXAMPLE 5

Multiparticulate ibuprofen tablet at a dose of 100 mg.

The composition of the above tablet results from Table VI below.

TABLE VI

| Constituents | Centesimal formula |
| --- | --- |
| Coated ibuprofen | 14.4 |
| Mannitol for direct compression | 52.5 |
| Crystalline powder mannitol | 17.5 |
| Crospovidone | 10.0 |
| Aspartame | 3.7 |
| Cherry flavouring | 0.9 |
| Magnesium stearate | 1.0 |
| Total | 100.0% |

This tablet is prepared in the manner indicated in Example 1.

The ibuprofen microcrystals having an average size in the region of 30 micrometres are granulated by a standard wet route granulation process. The resulting particle is then coated with 20% of a mixture of ethyl cellulose N7 and polyethyleneglycol 6000.

The resulting coated ibuprofen crystals are mixed with the excipient, then subjected to compression.

The resulting tablet has a hardness of 40±10 Newtons.

It disintegrates in the mouth in 30 seconds.

What is claimed is:

1. A multiparticulate tablet disintegrating in the mouth in less than 40 seconds and comprising an excipient and an active ingredient in the form of microcrystals comprising a taste-making coating wherein the excipient comprises, with respect to the mass of the tablet, from 3 to 15% by weight of at least one disintegration agent selected from the group consisting of cross-linked polyvinylpyrrolidone and cross-linked carboxymethylcellulose and from 40 to 90% by weight of at least one soluble diluent agent with binding properties consisting of a polyol having less than 13 carbon atoms, said polyol being either in the directly compressible form which is composed of particles whose average diameter is from 100 to 500 micrometers or in the powder form which is composed of particles whose average diameter is less than 100 micrometers, said polyol being selected from the group consisting of mannitol, xylitol, sorbitol and maltitol, with the proviso that, when only one soluble diluent agent with binding properties is used, it is a polyol in the directly compressible form except sorbitol and, when at least two soluble diluent agents with binding properties are used, these are consisting of the same polyol, one part of which is in the directly compressible form while the other part is in powder form, the proportion of directly compressible polyol to powder polyol being from 99/1 to 50/50 and the coating of the microcrystals of active ingredient comprises at least one coating agent selected as a function of the physico-chemical characteristics of the active ingredient selected from the group consisting of polymethacrylates and cellulose polymers and combinations thereof with each other.

2. A multiparticulate tablet according to claim 1, wherein the proportion of disintegrating agent and of soluble diluent agent with binding properties is respectively from 5 to 10% and from 50 to 70% by weight.

3. A multiparticulate tablet according to one of claim 1 or 2, wherein the maximum proportion of sorbitol is 30% by weight.

4. A multiparticulate tablet according to claim 1, wherein the proportion of directly compressible polyol to powder polyol is from 80/20 to 50/50.

5. A multiparticulate tablet according to claim 1, wherein the coating agent is selected from the group consisting of hydroxypropyl-methyl cellulose, hydroxypropyl cellulose and cellulose acetophthalates.

6. A multiparticulate tablet according to claim 1, wherein the coating agent is combined with at least one of the products of the group consisting of plasticizers, soluble agents and polyols.

7. A multiparticulate tablet according to claim 1, wherein the bioavailability of the active ingredient is at least equivalent to that of the active ingredient of the same tablet wherein the said active ingredient is not coated, allowing thus its immediate release.

8. A multiparticulate tablet according to claim 7, wherein the quantity of active ingredient which is dissolved from the coated microcrystals, after disintegration of the tablet, in 5 to 20 minutes when placed in an acid medium having a pH lower than 5, is equal to at least 80% of the quantity of active ingredient which is dissolved in the same time after disintegration from a tablet which is identical except the fact that the microcrystals are not coated.

9. A multiparticulate tablet according to claim 7, wherein the quantity of active ingredient which is dissolved from the coated microcrystals, after disintegration of the tablet, in 5 to 20 minutes when placed in an acid medium having a pH lower than 5, is equal to at least 100% of the quantity of active ingredient which is dissolved in the same time after disintegration from a tablet which is identical except the fact that the microcrystals are not coated.

10. A multiparticulate tablet according to one of claims 7 to 9, wherein the active ingredient does not dissolve significantly after remaining for a period of less than 5 minutes in a medium the pH conditions of which is 7.0±0.5, thus providing satisfactory masking of the taste.

11. A multiparticulate tablet according to claim 1, wherein the active ingredient is selected from the group consisting of analgesics, antipyretics, antidiarrheals, antispasmodics, digestive motoricity regulators and anti-inflammatories.

12. A multiparticulate tablet according to claim 1, wherein the active ingredient is selected from the group consisting of paracetamol, ibuprofen, aspirin, ketoprofen and loperamide.

* * * * *